United States Patent [19]

Schobel et al.

[11] Patent Number: 4,671,972
[45] Date of Patent: * Jun. 9, 1987

[54] CONTROLLED RELEASE ENCAPSULATED HYPOCHLORITE DEACTIVATOR FOR USE IN DENTURE CLEANSERS

[75] Inventors: Alexander M. Schobel, North Plainfield; Robert W. Schumacher, Kenvil, both of N.J.

[73] Assignee: Warner-Lambert Company, Morris Plains, N.J.

[*] Notice: The portion of the term of this patent subsequent to Nov. 12, 2002 has been disclaimed.

[21] Appl. No.: 773,760

[22] Filed: Oct. 9, 1985

Related U.S. Application Data

[63] Continuation of Ser. No. 590,129, Mar. 16, 1984, Pat. No. 4,552,679.

[51] Int. Cl.$^4$ .......................... A61K 7/30; C11D 7/54; C11D 7/60; C11D 17/00
[52] U.S. Cl. ..................................... 427/213; 252/90; 252/95; 252/99; 252/174.13; 252/174.17; 252/186.26; 252/186.31; 427/212; 427/221
[58] Field of Search ..................... 252/90, 95, 99, 105, 252/174, 174.12, 174.13, 174.17, 174.23, 186.3, 186.31; 427/221, 213, 215, 212

[56] References Cited

U.S. PATENT DOCUMENTS

| | | | |
|---|---|---|---|
| 3,042,621 | 7/1962 | Kirschenbauer | 252/99 |
| 3,723,327 | 3/1973 | van Kampen | 252/110 |
| 3,821,117 | 6/1974 | Breece | 252/99 |
| 3,893,954 | 7/1975 | Tivin | 252/548 |
| 3,936,385 | 2/1976 | Cheng | 252/99 |
| 3,962,107 | 6/1976 | Levin | 252/100 |
| 3,975,280 | 8/1976 | Brichard | 252/186 |
| 3,997,459 | 12/1976 | Bogie | 252/99 |
| 4,256,599 | 3/1981 | Krisp | 252/99 |
| 4,295,985 | 10/1981 | Petrow | 252/105 |
| 4,327,151 | 4/1982 | Mazzola | 428/407 |
| 4,362,639 | 12/1982 | Eoga | 252/99 |
| 4,417,993 | 11/1983 | Gergely | 252/90 |
| 4,421,664 | 12/1983 | Anderson | 252/94 |
| 4,457,858 | 7/1984 | Saran | 252/99 |

FOREIGN PATENT DOCUMENTS 7305291 10/1973 Netherlands.

OTHER PUBLICATIONS

I. Weil and J. C. Morris, "Kinetic Studies on the Chloramines", *J. Am. Chem. Soc.*, 1949, 71, 1664–1671.

R. E. Connick, "The Interaction of Hydrogen Peroxide and Hypochlorous Acid in Acidic Solutions Containing Chloride Ion", *J. Am. Chem. Soc.*, 1947, 69, 1509–1514.

M. W. Lister & P. Rosenblum, "The Oxidation of Nitrate and Iodate Ions by Hypochlorite Ions", *Canadian Journal of Chemistry*, 1961, 39, 1645–1651.

*Primary Examiner*—Dennis L. Albrecht
*Attorney, Agent, or Firm*—Charles A. Gaglia, Jr.; Gary M. Nath

[57] ABSTRACT

A denture cleansing composition of the hypochlorite type is rendered substantially free of hypochlorite chlorine odor by incorporating into the composition a hypochlorite deactivator. The deactivator is released into the cleansing solution at a controlled rate to optimize cleansing efficacy at a reduced hypochlorite/chlorine odor. The deactivators suitable for use in this invention include sodium perborate monohydrate and sodium nitrite. The preferred method of controlling deactivator release rate is by encapsulating the deactivator.

14 Claims, 1 Drawing Figure

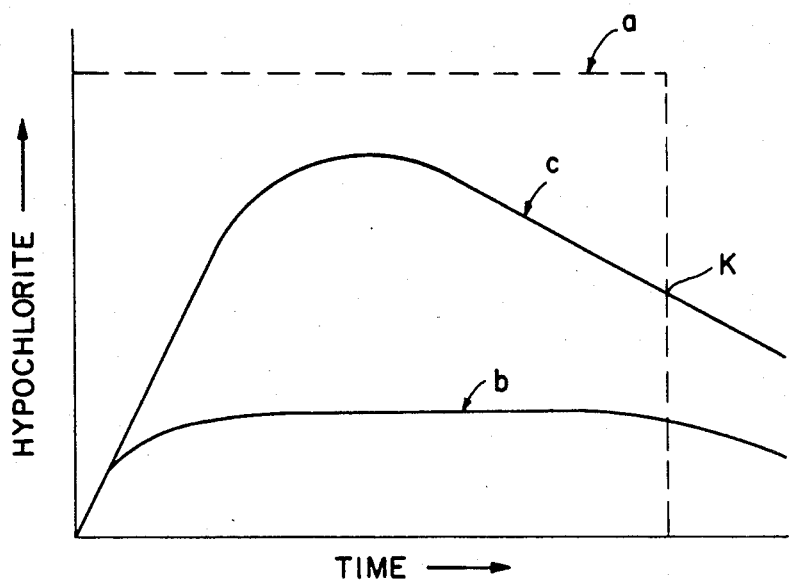

CONTROLLED RELEASE ENCAPSULATED HYPOCHLORITE DEACTIVATOR FOR USE IN DENTURE CLEANSERS

This is a continuation of application Ser. No. 590,129 filed Mar. 16, 1984, now U.S. Pat. No. 4,552,679.

FIELD OF THE INVENTION

This invention relates to a denture cleansing composition comprising a hypochlorite generating agent and a hypochlorite deactivator which is substantially free of chlorine odor. More particularly it relates to a hypochlorite type denture cleansing composition having incorporated therein a controlled release deactivator for the hypochlorite.

BACKGROUND OF THE INVENTION

Effervescent denture cleansers have been long known in the art. Most of those presently on the market derive their cleansing efficiency mainly from peroxy compounds which provide active oxygen. While the active oxygen provides a good bleaching action, it has relatively poor plaque removing properties. Various peroxygen type denture cleansers are described in U.S. Pat. Nos. 2,498,343; 2,498,344; 2,931,776 and 3,243,377.

Another type of denture cleanser described in U.S. Pat. No. 3,113,111 derives its cleansing efficacy from an active chloride source and has good plaque removing properties. The product, however, is not effervescent and must be stirred mechanically to dissolve. An effervescent denture cleansing composition which releases hypochlorite/chlorine on contact with water is disclosed in U.S. Pat. No. 3,936,385. The product has good plaque removing properties and dissolves without stirring. However, it is not fully acceptable because of the chlorine odor associated with the product and its tendancy to corrode metals. Efforts to mask odor using fragrances have been unsuccessful because of the strong hypochlorite odor.

Recent improvements in these hypochlorite type of denture cleansing composition include the disclosure of U.S. Pat. No. 4,362,639 to Eoga. The denture cleanser of that disclosure include ammonium ion compounds which inhibit hypochlorite odor emission and inhibit metal tarnish or corrosion. However, amine compounds may result in the generation of undesirable chloramines.

The art is replete with references which teach the reaction of hypochlorite solutions with a wide range of compounds. An article entitled "Kinetic Studies on the Chloramines," authored by Ira Weil and J. Carrell Morris, *J. Am. Chem. Soc,* 71, 1644–1671 (1949) discloses reactions of ammonia and primary amines witn hypochlorite. The reaction of hydrogen peroxide and hypochlorous acid has been studied; see for example "The Interaction of Hydrogen Peroxide and Hypochlorous Acid in Acidic Solutions Containing Chloride Ion ", Connick, R. R., *J. Am. Chem. Soc.,* 69, 1509–1514 (1947). Similarly the reactions of iodates and nitrites are taugnt in the art; see "The Oxidation of Nitrite and Iodate Ions by Hypochlorite Ions," Lister, M. W. and Rosenblum, P., *Canadian Journal of Chemistry,* 39, 1645–1651 (1961). Hydrazine dihydrochloride has been taught as a chlorine scavenger. See "Chlorine Scavenger for HCL Gas Streams," page 539 Merck Index 8th Ed., 1968. Guanidine has also been used to scavenge chloride in sewer gases.

U.S Pat. No. 4,295,985 discloses a soap which removes chlorine odor from the skin and hair of bathers. The composition is said to neutralize chlorine (as hypochlorite). Compounds taught to be suitable neutralizing agents are sodium nitrite, sodium sulfite, sodium thiosulfate, urea, thiourea, ascorbic acid, hydrazine, hydroxylamine, pyrrole, sodium terrocyanide, hydroquinone, formaldehyde, furtural, sodium hypophosphate and sodium hydrosulfite.

In general, the prior art approach has been to add the deodorizing agent to the denture cleansing composition. As such, it immediately begins to reduce the available hypochlorite. Hence, either reduced efficiency must be accepted or substantially larger amounts of cleansing agent, at increased costs, must be utilized to achieve the desired effect.

Various methods are taught in the art for delaying the activity of a particular component of the denture cleansing composition. For example, U.S. Pat. No. 3,952,107 discloses a two part tablet which preferentially releases an enzyme to attack the proteinaceous materials which are loosely bonded to plaque. Subsequently, an oxygen generating agent is released to complete the cleaning. The delay time between each activation step is disclosed to be about 60 to 120 seconds. The time release is accomplished by consideration of the relative thickness of the two layers, the proportion of the effervescent producing composition in each layer and the particle size of certain ingredients in each layer. Similarly, U.S. Pat. No. 4,256,999, discloses a two layer denture cleansing tablet, each of which disintegrate at controlled rates to give improved cleaning efficiency. Various techniques, including the use of silicic acid and polyvinyl pyrrolidone, to control the release rate are taught.

There is no teaching in the art of a method for preparing a substantially odor free, hypochlorite releasing denture cleanser.

SUMMARY OF THE INVENTION

It has surprisingly been found that a hypochlorite generating type denture cleansing composition can be rendered free of objectionable hypochlorite derived odor without loss of cleansing efficiency by incorporating into the composition a hypochlorite deactivator, the activation of which is controlled to minimize any deleterious effect on cleansing.

Controlled release of the deactivator compound is accomplished either by incorporating it into a two part tablet or by encapsulating the deactivator to form controlled released microcapsules.

BRIEF DESCRIPTION OF THE DRAWING

FIGURE—Hypochlorite elimination by deactivator as a function of time.

DETAILED DESCRIPTION OF THE INVENTION

This invention relates to a hypochlorite generating type of denture cleansing agent. More particularly it relates to an effervescent denture cleanser which utilizes a hypochlorite generating compound as a plaque removal agent. Specifically it relates to a method for rendering the hypochlorite cleansing composition free of objectional odor without loss of efficiency of the cleansing agent. This end is accomplished by incorporating into the denture cleansing composition a hypochlorite deactivator which is activated by controlled release over the cleansing cycle.

As used in the specification and claims the term "denture" means all those removable orthodontic appliances such as false teeth, dental plates and bridges. As used in the specification and claims the term "hypochlorite deactivator" means a compound which will react with a hypochlorite in solution to neutralize hypochlorite/chlorine odor.

In the practice of this invention any compound known to react with a hypochlorite can be used as the hypochlorite deactivator. Illustrative, non-limiting examples of suitable hypochlorite deactivators are sodium nitrite, potassium nitrite, sodium sulfite, sodium thiosulfate, urea, thiourea, ascorbic acid, hydroxylamine, pyrrole, sodium ferrocyanide, hydroquinone, formaldehyde, furfural, sodium hypophosphate, guanidine, sodium percarbonate, sodium perborate monohydrate, ammonium citrate, ammonium phosphate dibasic, ammonium peroxy disulfate, ammonium sulfate, ammonium thiosulfate, citric acid, sulfamic acid, ferrous sulfate, nickel hydroxide, guanidine, hydrazine, its derivatives and acid salts, lead sulfate, magnesium chloride, alkali metal sulfides and phosphites, etc.

While all of these compounds have at least a degree of effectiveness, most are not practical to use. As has been stated earlier, the ammonium compounds form chloramines. The sulfur compounds replace the chlorine odor with their own sulfurous odor and percarbonates are not cost effective. Hence, the preferred hypochlorite deactivators are alkali metal perborates, alkali metal nitrites, and ascorbic acid, with preferred alkali metals being sodium and potassium.

As used in the specification and claims, the term "hypochlorite generating agent" means any compound which upon contact with water generates or releases hypochlorite ion directly or by the interaction of two or more compounds. Illustrative, non-limiting examples of the hypochlorite generating agent of this invention are heterocyclic N-chloroimides such as a chloroisocyanurate, e.g., sodium dichloroisocyanurate, potassium dichloroisocyanurate, or trichlorocyanuric acid; complex salts of two or more compounds, e.g., [(mono-tri-chloro)-tetra(monopotassiumdichloro)]penta-isocyanurate; other N-chloroimides, e.g., sodium-p-toluene-sulfonochloramide, N,N-dichloro-p-toluenesulfonamide, sodium benzene-sulfonchloramide, N,N-dichlorobenzene-sulfonamide, N-chlorosuccinate. Still other compounds which liberate hypochlorite/chlorine on contact with water are N-chloro malonimide, N-chloro phthalinide and N-chloro naphthalimide; the hydantoins such as 1,3-dichloro-5,5-dimethyl hydrantoin; N-monochloro-C,C-dimethylhycrantoin; methylene-bis-(N-chloro-C,C-dimethylhydantoin); 1,3-dichloro-5-ethylhydantoin and 1,3-dichloro-5,5-diisoethylhydantoin; dry solid inorganic compound such as lithium hypochlorite, calcium hypochlorite; mixtures of salts, such as sodium persulfate and sodium chloride; sodium perborate and chlorinated 5-triazine triones.

In order to utilize the hypochlorite deactivator without adversely effecting the effectiveness of the hypochlorite as a cleansing agent it is necessary to delay the action of the deactivator until the cleansing action is complete. Otherwise, the deactivator will be destroying hypochlorite which is necessary for cleansing the denture. Generally, the cleansing action is complete in about 8 to about 20 minutes; and preferably about 10 to about 18 minutes.

The action of the hypochlorite deactivator can be controlled in one of two ways:

1. A two part tablet may be used having a first part which contains the cleansing agent and a second part which contains the hypochlorite deactivator. The second part of the tablet is formulated to disintegrate at a slower rate than the hypochlorite generating first part; and 2. The hypochlorite deactivator is encapsulated into microcapsules which are formulated to control the release of the deactivator over the cleansing cycle.

In preparing the two part tablets of this invention any of the prior art techniques such as those disclosed in U.S. Pat. No. 4,256,599 can be utilized for example, the two part tablet may consist of two tablets of equal diameter bonded together, one layer of the tablet containing the hypochlorite generating compound and the other layer, the hypochlorite deactivator. Alternately, a "sandwich" type of tablet may be used. The center section of the sandwich, containing the hypochlorite deactivator, is sandwiched between two layers of compound containing the hypochlorite generating agent. In another embodiment a tablet comprising the hypochlorite deactivator is completely encapsulated by a surrounding layer which comprises the hypochlorite generating agent. No part of the hypochlorite deactivator containing tablet remains exposed.

In order to control the release of deactivator into the cleansing solution the disintegration rate of the tablet is controlled. This is accomplished by adjusting the amount of the effervescent agent used in the tablet. The term "effervescent agent" means a compound utilized to cause the denture cleaning composition to effervesce resulting in disintegration of the capsule. Illustrative, non-limiting examples of effervescent agents are anhydrous sodium perborate; sodium perborate monohydrate; a mixture of an alkali metal bicarbonate and a water soluble organic acid, e.g., sodium bicarbonate, ammonium bicarbonate, potassium bicarbonate, citric acid, ascorbic acid and tartaric acid.

Where the effervescent agent is a mixture of an alkali metal bicarbonate and an organic acid it is used at about 20% to about 40% (w/w) based on the total weight of the tablet composition. Where the effervescent agent is a perborate it is utilized at about 15% to about 20% (w/w) based on the total weight of the tablet.

Sulfamic acid is both an effervescent agent and a hypochlorite deactivator. Where sulfamic acid is used as the deactivator no additional effervescent agent is required. Its concentration in the tablet is determined by its requirement as a deactivator.

An alternative method of controlling release of hypochlorite deactivator is by encapsulation of the deactivator in a film forming material which will control the rate of release at a rate which does not adversely affect the cleansing action of the hypochlorite.

Ideally, in both the encapsulation and two part tablet method of controlled release, no deactivator will be made available until the entire cleansing cycle is complete. It will be appreciated by those skilled in the art that in the time frame of the denture cleansing cycle, about 8 to about 20 minutes, it is not possible to accomplish that end. Hence, the ideal must be approximated by controlling the rate of release of deactivator so as not to consume so much hypochlorite as to adversely affect the cleansing action. This concept will be more readily appreciated by reference to the FIGURE.

Referring now to the FIGURE curve "a" represents the idealized hypochlorite concentration curve over a denture cleansing cycle t. The hypochlorite instantaneously reaches its maximum value and is immediately eliminated at the end of the cleansing cycle by the subsequent release of deactivator. Prior art methods of including a hypochlorite deactivator in the denture cleansing composition result in a hypochlorite concentration curve represented by curve "b." The hypochlorite is maintained at a low level throughout the cleansing cycle. Hence, cleansing efficiency is greatly reduced. Curve "c" represents the results achieved by the method of this invention where k is the available hypochlorite concentration at end of the cleaning cycle. Ideally, k is zero. However, time and economic constraints require that k be fixed at some acceptable level which will permit hypochlorite derived odor to be masked by an acceptable fragrance.

It is necessary that not only the odor of the solution, but the odor produced upon the reaction of hypochlorite ion with the proteinaceous material, e.g., the skin of the fingers and hand, be eliminated. It is this latter odor which is of primary concern since the solution odor is only mildly objectionable. The term "hypochlorite derived odor" as used in the specification and claims means solution odor as well as odor resulting from the attack of hypochlorite on proteinaceous material. The value of "k" is not itself significant since the test of an acceptable odor is a subjective one which must be determined by correlating product parameters with the perceived results as evaluated by users of the product.

Any of the commercially available spray dried fragrances are suitable for the practice of this invention. The spray dried fragrances comprise a fragrance oil which has been deposited on a solid, such as maltodextrin, by a solution spray drying technique. Illustrative, non-limiting examples of spray dried fragrances which can be used in the practice of this invention are peppermint, wintergreen, lime, lemon, menthol, and so forth. While the amount of fragrance used is a matter of choice at least 0.1% (w/w) based on the total denture cleansing composition should be used in order to mask the hypochlorite-chlorine odor.

Tablet Method

In preparing a two part tablet a first part, which is the cleaning composition, is prepared and a second part, which contains the deactivator, is formulated to counteract the stoichiometric amount of hypochlorite which will be released. It will be appreciated that while the term "stoichiometric amount" has a precise meaning for the chemist, as used in the specification and claims, it means an amount which approximates the stoichiometric amount of deactivator required to react with all of the hypochlorite released into the solution. Since other components of the cleansing composition, e.g., perborate, can deactivate hypochlorite an amount which is less than the stoichiometric amount depending on the amount of perborate, for example, can be used. Similarly, more than the stoichiometric amount may be utilized, but no benefit is seen in the use of excess deactivator. Generally, however, the calculated stoichiometric amount of deactivator required to deactivate the hypochlorite will be used to insure that all of the hypochlorite is deactivated.

Any hypochlorite generating denture cleansing composition of the prior art can be used in the practice of this invention. A typical formulation is shown in Table I. The amounts indicated are sufficient to make 1000 tablets each having a weight of 2.89 grams.

TABLE I

| HYPOCHLORITE DENTURE CLEANSER | |
|---|---|
| Component | Weight (grams) |
| Sodium Bicarbonate | 285.0 |
| Sodium Sulfate | 90.0 |
| Citric Acid | 190.0 |
| Sodium Carbonate | 1450.0 |
| Ethylenediaminetetraacetic acid tetra sodium salt | 60.0 |
| Sodium Perborate, Monohydrate | 240.0 |
| Sodium Dichloroisocyanurate | 560.0 |
| Detergent | 15.0 |
| Magnesium Stearate | 4.0 |

EXAMPLE 1

Tablets were formed using the composition set forth in Table I. Tableting was accomplished on a Stokes Rotary Press with flat faced bevel edged tooling (FFBE). The tablets had a hardness of 12–15 S.C.U. after curing to remove excess water.

Separate tablets were prepared using ammonium phosphate, urea and sulfamic acid as the hypochlorite deactivator. Release rate was controlled by fixing the amount of material used to cause effervescence thereby controlling the rate of break up of the tablet. Table II shows various compositions of the second part tablet. Runs A and B utilized sodium bicarbonate and citric acid in a stoichiometric amounts relative to one another in order to disintegrate the tablet. Run C uses sulfamic acid as both the effervescent agent and the hypochlorite deactivator. Fortuitously, the amount required for deactivation is also correct for tablet disintegration. About 20% to about 30% (w/w) of sulfamic acid based on the total weight of the tablet is sufficient as an effervescent agent. The amount of sulfamic acid must be balanced (stoichiometrically) against the quantity of hypochlorite generating agent used.

TABLE II

| HYPOCHLORITE DEACTIVATOR TABLET | | | |
|---|---|---|---|
| | Run | | |
| | A[1] | B[2] | C[3] |
| Ammonium Phosphate | 75 | — | — |
| Urea | — | 28.75 | — |
| Sulfamic Acid | — | — | 75 |
| Sodium Bicarbonate | 71.0 | 107.0 | — |
| Citric Acid | 54.0 | 81.0 | — |
| Sodium Sulfate | 292.0 | 275.0 | 225.0 |
| Polytetrafluoroethylene Powder | 7.5 | 7.5 | 7.5 |

[1] grams for 250, 2.0 gm tablets at 5 to 7 SCU using FFBE tool
[2] grams for 250, 2.0 gm tablets at 7 to 8 SCU using FFBE tool
[3] grams for 250, 2.0 gm tablets at 10 to 11 SCU using FFBE tool The tablets of the formulations of Runs A, B and C were each tested with a tablet prepared according to the formulation of Table I both as a single two part tablet and as individual tablets. The tablets were dissolved in 125 ml of water at 45° C. The tablet of Run A disintegrated over a 12–15 minute period, while the tablet of Run B disintegrated over a 12 minute period. The tablet of Run C disintegrated over a 12–15 minute period. Cleaning was effective and at the conclusion of the test the solution and plaque coated test tiles were odor free. Furthermore, a finger dipped into the solution did not have any objectional odor. The results would be the same when the tablets of Runs A, B and C were compressed with the tablet of Table I into a unitary structure. Test tiles were prepared by growing plaque on one side of 1×¾ in. tile and staining the tiles overnight with a mixture of coffee, tea, blueberry pie filling and grape juice.

As used in the specification and claims, the term "two part tablet" means a single tablet pressed together comprising a first part of hypochlorite denture cleanser and a second part comprising hypochlorite deactivator, as well as a two tablet system wherein one tablet comprises the hypochlorite cleanser and the other tablet comprises the hypochlorite deactivator.

Encapsulation Method

In a preferred embodiment, the hypochlorite deactivator is encapsulated in a barrier film which controls the rate of dissolution of the hypochlorite deactivator in the denture cleaning solution. While the encapsulation technique used in the practice of this invention is well known in the art, there are certain parameters which are critical to the successful encapsulation of a hypochlorite deactivator which is effective for the purpose of this invention. These parameters include selection of the coating material, particle size of the hypochlorite deactivator, weight percent of coating material relative to deactivator weight, the method of application of coating material and the amount of plasticizer used in the encapsulating film.

The hypochlorite deactivator may be utilized in either bead or granule form. However, it should have a particle size of less than 20 mesh to about 50 mesh (U.S. standard stainless steel mesh). The appropriate particle size may be selected by sieving the deactivator and rejecting material which is collected on a 20 mesh screen and which passes through a 60 mesh screen. Particles larger than about 20 mesh cannot be used since they create problems in the feeder and hopper or the tabletting machine, e.g., segregation. At a particle size substantially smaller than 50 mesh the particles have too large a surface area and encapsulation becomes uneconomical because of the large quantities of encapsulating material required.

The encapsulating material must be used at about 6% to about 20% by weight based on the total weight of the encapsulated deactivator particle, preferably about 12% to about 20%, and more preferably about 14% to about 20%. At less than 6% by weight of coating of encapsulating material the deactivator dissolves too quickly in the hypochlorite denture cleanser solution resulting in insufficient hypochlorite being available for cleaning. At above about 20% by weight of the coating of encapsulating material the dissolution rate is too slow to be of any value from a practical cleaning cycle standpoint.

The coating can be applied either from a solution or an emulsion. In applying the coating during the encapsulation process, the solids content of the vehicle should be about 6 to about 30% (w/w) based on the total weight of vehicle plus coating. Below 6% solids inordinately long times are required to apply the coating. At high solids content, i.e. greater than 30% (w/w), the solution or emulsion was either too viscous or the coatings were not uniform.

A plasticizer is required for the coating to ensure good film-forming characteristics. Excessive amounts of plasticizer results in stickiness and agglomeration of coated particles. Too low a level results in a discontinuous coating and as a consequence immediate dissolution of deactivator. While the preferred range of plasticizer will depend on the specific film forming material utilized, about 18% to about 40% (w/w) based on the film former solids can be used, preferably about 20% to about 30% (w/w). It should be noted that reference to coating weight includes film former, plasticizers and adjunctives which may be included in the coating formulation.

The type of plasticizer used will depend on the selection of film former. Specific plasticizers are normally recommended by the film former supplier and no advantage is seen in deviating from these recommendations. Where the film former is ethyl cellulose the recommended plasticizer is dibutyl sebacate. Triethyl citrate can also be used.

The film former must not be water soluble. Since the pH of denture cleansing solutions is at least 7.5 and preferably about 8.5 to 11.0, e.g. 9.0 to 10.0, the film former must not be solubilized by basic solutions. Hence, the enteric coatings normally used for drugs are ineffective. The film former must, therefore, be water insoluble. Furthermore, it must either be permeable with respect to $H_2O$ and nitrite ions, or adjunctives which are water soluble or hydrophilic must be included in the film. The latter technique is well known in the art. For example, water soluble polymers such as polyvinyl alcohol can be incorporated into the coating at about 2% to about 10% by weight. Alternatively, the adjunctive can be a water insoluble material rendered soluble at high pH, e.g. polyvinyl acetate phthalate (PVAP) or butyrate (PVAB). The film former is preferably swelled by water.

PVAB and PVAP may be utilized as the film former at coating weights of about 25 to about 30% (w/w). The preferred film former is ethyl cellulose. Other film formers which may be utilized either directly or with the aid of adjunctives are styrene-maleic anhydride copolymers and sulfonated polystyrene wherein the sulfonation comprises less than 15 mole % of the polymer e.g. 5-10 mole %. Other sulfonated polymers such as sulfonated ethylene-propylene-terpolymers (EPDM), with the same caveat as to degree of sulfonatin, and polyvinyl acrylate may be used.

The method of encapsulation is well known to those skilled in the art and can be accomplished with known techniques. Those skilled in the art will recognize that the objective is to produce a dry, non-tacky coated product, and therefore, will appreciate what process parameters are required to achieve that end.

The film former is preferably applied by spraying a solution or emulsion into the air inlet stream of a fluidized bed comprising the particles to be coated. To ensure evaporation of the vehicle the inlet air temperature should be about room temperature 23° C., to about 65° C.

Sufficient air flow is required to fluidize the particles so that a "boiling bed" condition exists. The air flow rate will depend on the bed height (charge) and particle density. As those skilled in the fluidization art will recognize, the flow rate must be sufficient so that the pressure drop through the bed exceeds the bed weight per unit area. However, excessive flow rates are to be avoided to minimize attrition or fracture of particles. An air flow rate of about 30 to about 80 m³/hr has been found to be adequate, preferably the air flow rate is about 55 to about 75 m³/hr.

It has been found that in order for the coated particles to be compressible without damage it is necessary to cure the coated particles at about 85° C. to 100° C. for about 45 minutes to about 75 minutes, preferably about 90° C. for about 55 to 65 minutes. Lower temperatures are ineffective and higher temperatures adversely affect the film stability. As used in the specification and claims the term "coating medium" means the film former, plasticizers and adjunctives in a solvent or as an emulsion.

The encapsulation process of this invention is illustrated by the following examples.

EXAMPLE II

Coating of NaNO$_2$

Particles of NaNO$_2$ in the 20 to 50 mesh range were coated with a plasticized film of ethyl cellulose. The air inlet temperature was room temperature and the carrier air flow rate was 55/m$^3$/hr. The coating medium was introduced to the unit at 5 ml/min. The product was dried in the column for about 15 min. at 65° C. and subsequently cured at about 90°–95° C. for one hour. The coating weight was 8% (w/w) based on the NaNO$_2$. The coating medium had the following formulation:

| Coating Solution | w/w % |
|---|---|
| Ethyl Cellulose | 5.0 |
| Dibutyl Sebacate | 1.0 |
| Stearyl dimethyl benzyl NH$_4$Cl | 0.25 |
| Ethanol | 93.75 |

Approximately 0.400 Kg of material was coated using about 0.65 Kg of solution.

EXAMPLE III

The method of Example II was repeated using 0.200 Kg of NaNO$_2$. The inlet air temperature was 60° C. and the fluidizing air flow rate was 75 m$^3$/hr. Instead of an alcohol solution the coating was applied from an emulsion which included an ethyl cellulose latex emulsion (30% solids). The formulation of the coating medium was as follows:

| Component | w/w % |
|---|---|
| Ethyl Cellulose latex emulsion | 50.00 |
| Dibutyl Sebacate | 3.00 |
| Deionized Water | 46.965 |
| Talc | 0.035 |

The finished product comprised a coating of 15.25% (w/w) based on the NaNO$_2$. The product was oven dried for 1 hour at 90° C.

EXAMPLE IV

Example II was repeated using 0.400 Kg of sodium perborate, monohydrate. The fluidizing air flow rate was 32 m$^3$/hr and the spray rate was 8 ml/min sustained for 65 minutes. The formulation of the coating medium was as follows:

| Component | w/w % |
|---|---|
| Ethyl Cellulose | 5.0 |
| Dibutyl Sebacate | 1.0 |
| Ethanol, Anhydrous | 94.0 |

EXAMPLE V

Tablets were prepared using the compositions shown in Table III incorporating sodium dichloroisocyanate as the hypochlorite generating agent and the deactivators of Examples II, III and IV. The amount of deactivator used is the stoichiometric amount with respect to the amount of dichloroisocyanurate.

TABLE III

| TABLET COMPOSITION | A[1] mg/tab | B mg/tab | C mg/tab |
|---|---|---|---|
| Sodium Bicarbonate | 285 | 285 | 285 |
| Sodium Sulfate | 90 | 90 | 90 |
| Citric Acid | 190 | 190 | 190 |
| Sodium Carbonate | 1450 | 1450 | 1450 |
| Ethylenediaminetetraacetic Acid, Na$_4$.salt | 60 | 60 | 60 |
| Sodium Dichloroisocyanurate | 560 | 560 | 560 |
| Sodium Perborate Monohydrate | 240 | 240 | 240 |
| Detergent | 15 | 15 | 15 |
| Magnesium Stearate | 10 | 10 | 10 |
| Coated Na Perborate H$_2$O (Example IV) | 270[2] | — | — |
| Coated NaNO$_2$ ("A") (Example II) | — | 380.43[2] | — |
| Coated NaNO$_2$ ("B") (Example III) | — | — | 413.12[2] |

[1] The weights shown are the amounts to prepare one tablet having a total weight (mg) as shown.
[2] Weight is total weight of coated particle.

The best overall results were achieved with the NaNO$_2$ having a coating weight of 15.28% (w/w).

EXAMPLE VI

Example III was repeated and encapsulated NaNO$_2$ having coating weights (% w/w) of 6, 8, 10, 12, 14, 16, and 20%. Tablets were prepared using the formulation of Run C of Table III, Example V. The total weight of encapsulated deactivator was adjusted to compensate for coating weight thereby ensuring that a stoichiometric amount of deactivator was present.

The effectiveness of each of the compositions was evaluated by testing the odor characteristics and cleansing efficacy of each. Tests subjects were asked to evaluate the objectionability of hypochlorite derived odor from the solution and on the skin. All of the compositions were acceptable from the standpoint of hypochlorite derived odor.

Cleansing efficacy was found to be marginal below 12 weight percent of coating. Optimum results were achieved at a coating weight of 18%. At 20% there was no substantial improvement in cleaning over the 18% coating which would not justify the increased cost of coating.

It was found that from the standpoint of cleansing efficacy and solution odor the optimum results were achieved with the 18% (w/w) coating. While lighter coatings resulted in reduced odor they also resulted in poorer cleaning. At 18% (w/w) coating the odor was sufficiently reduced to be masked by a spray-dried peppermint fragrance.

The invention being thus described, it will be obvious that the same may be varied in many ways. Such variations are not to be regarded as a departure from the spirit of scope of the invention and all such modifications are intended to be included within the scope of the claims.

What is claimed is:

1. A controlled release encapsulated hypochlorite deactivator composition comprising:
    (a) a hypochlorite deactivator having a particle size of about 20 mesh to about 50 mesh; and (b) a coating composition completely surrounding and enclosing the deactivator said coating composition comprising:
  (1) a water insoluble, pH insensitive film forming composition wherein said film forming composition is ethylcellulose, and
  (2) a plasticizer in an amount from about 18% to about 40% by weight based on the total weight of the coating composition wherein the coating composition comprises about 6% to about 20% (w/w) of the encapsulated deactivator.

2. The deactivator composition according to claim 1 wherein the hypochlorite deactivator is an alkali metal perborate, alkali metal nitrite, or ascorbic acid.

3. The composition according to claim 2 wherein the alkali metal is sodium.

4. The composition according to claim 2 wherein the film forming composition is ethylcellulose, the alkali metal is sodium, the plasticizer is dibutyl sebacate, and the coating composition comprises 18% (w/w) of the encapsulated deactivator.

5. A process for preparing a controlled release encapsulated hypochlorite deactivator which comprises:
  (a) encapsulating the deactivator in a coating composition comprising a water permeable insoluble film forming composition wherein the film former is ethylcellulose and a plasticizer for the film forming composition said coating comprising about 6% to about 20% by weight of the encapsulated deactivator, based on the weight of deactivator, and said coating comprising about 18% to about 40% by weight of plasticizer based on the total weight of the coating composition; and
  (b) curing the encapsulated deactivator for about 45 minutes to about 75 minutes at a curing temperature of about 85° C. to about 100° C.

6. The process according to claim 5 wherein the film former is ethylcellulose and the plasticizer is dibutyl sebacate.

7. The process according to claim 5 wherein the plasticizer comprises about 20% to about 30% (w/w) of the coating.

8. The process according to claim 5 wherein the coating comprises about 18% by weight of the encapsulated deactivator based on the weight of deactivator.

9. The process according to claim 5 wherein the coating is applied by a fluidized bed spray coating process from a solution or emulsion of the coating composition.

10. The process according to claim 9 wherein the coating composition comprises about 6% solids to about 30% by weight of the solution or emulsion.

11. The process according to claim 10 wherein the coating emulsion comprises:
  (a) about 50% by weight of an ethylcellulose emulsion having a solids content of about 30% (w/w), based on the coating emulsion; and
  (b) about 3% by weight based on the coating emulsion of dibutyl sebacate.

12. The process according to claim 5 wherein the hypochlorite deactivator has a particle size range of about 20 mesh to about 50 mesh.

13. The process according to claim 5 wherein the hypochlorite deactivator is an alkali metal perborate, alkali metal nitrite, or ascorbic acid.

14. The process according to claim 13 wherein the deactivator is $NaNO_2$.

* * * * *